United States Patent [19]

Ronzi

[11] 4,196,726
[45] Apr. 8, 1980

[54] APPARATUS FOR DERMATOLOGICAL TREATMENT

[75] Inventor: Carl Ronzi, Zürich, Switzerland

[73] Assignee: Somartec S. A., Switzerland

[21] Appl. No.: 856,580

[22] Filed: Dec. 1, 1977

[30] Foreign Application Priority Data

Dec. 23, 1976 [DE] Fed. Rep. of Germany ....... 2658423

[51] Int. Cl.² ............................................ A61M 11/00
[52] U.S. Cl. ................................................ 128/207.27
[58] Field of Search ................. 128/65, 186, 190, 192, 128/254, 256, 399, 400, 172.1, 173.2

[56] References Cited

U.S. PATENT DOCUMENTS

| 1,351,012 | 8/1920 | Holmes | 128/192 |
| 2,095,651 | 10/1937 | Ronzi | 128/399 |
| 2,284,235 | 5/1942 | Ronzi | 128/173.2 X |
| 2,522,718 | 9/1950 | Huck | 128/192 X |
| 2,622,593 | 12/1952 | Peirano | 128/173.2 |
| 3,749,092 | 7/1973 | Williams | 128/256 |
| 4,026,285 | 5/1977 | Jackson | 128/192 |
| 4,028,445 | 6/1977 | Hickmann et al. | 128/173.2 X |

Primary Examiner—Richard J. Apley
Attorney, Agent, or Firm—Craig and Antonelli

[57] ABSTRACT

Apparatus for treating the skin with a spray of a mixture of water vapor and ozone gas. The apparatus has a spray nozzle connected to an ozone gas producer and to a water container provided with an evaporation device. In order to separate non-vaporous material, such as water droplets, from the water vapor, an expansion chamber is interposed between the water container and the nozzle.

4 Claims, 1 Drawing Figure

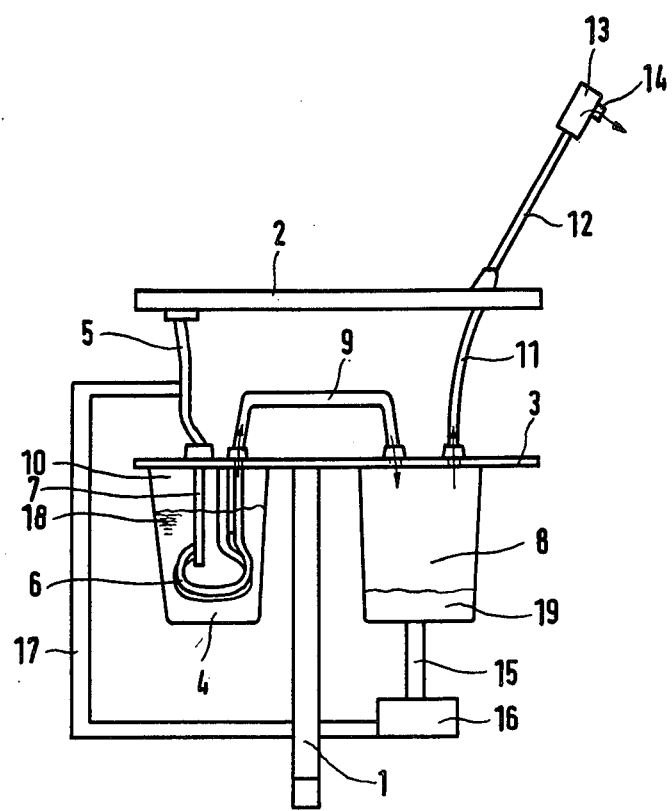

APPARATUS FOR DERMATOLOGICAL TREATMENT

This invention relates to apparatus, for cosmetic dermatological treatment with a water vapour ozone gas mixture, comprising a water container having an evaporation apparatus, an ozone gas producer, and a nozzle for spraying the water vapour/ozone gas mixture which nozzle is connected to a vapour chamber of the water container.

Such apparatus for dermatological treatment now constitutes standard equipment in the cosmetic field. The apparatus is used in particular for the treatment of the face, neck and the upper body/throat region. The ozone gas is usually produced in a chamber lying in front of the nozzle, for example, by means of a UV burner, whilst the vapour flows through a portion of this chamber and the ozone gas is taken along by injector action. The vapour stream enriched with air-ozone emerging from the nozzle is directed onto the part of the body to be treated.

The water vapour/ozone mixture tends to be directed as a greatly concentrated jet on the parts to be treated, but only a kind of vapour stream is in fact required. The outlet pressure must therefore be kept comparatively low. This fact, and the further requirement that the temperature should not be substantially above 100°, render the use of superheated steam impossible. Consequently condensation forms inside the whole vapour supply system which condensation in certain circumstances is expelled from the nozzle in the form of drops, or in consequence of a suction action as a stream, and reaches the parts of the body to be treated as hot water. This must be avoided. A further unpleasant effect arises from the fact that with the evaporation of the water impurities contained in the water, such as lime or the like, pass into the vapour supply system. If these impurities reach the region of the outlet nozzle then the apparatus "spits" which of course is undesirable. For this reason at least de-mineralised or better still distilled water must be used. In spite of this, however, in particular after lengthy operation, the disadvantageous effect described can still occur.

With the treatment described it is desirable to add to the water cosmetic material such as essential oils, etc. which are at least partly transmitted with the vapour onto the part of the body to be treated. Such an addition of materials can however be excluded in practice because these materials generally tend to foam with the consequence that this foam passes into the supply system and emerges at the nozzle. The undesired "spitting" of the apparatus can also occur for this reason.

An object of the present invention is to design an apparatus of the above mentioned kind such that the aforementioned problems can be overcome and, in particular, the introduction of cosmetic materials into the water vapour/-ozone mixture is rendered possible.

According to the invention therefore, between the water container and the nozzle of the apparatus there is disposed an expansion chamber or separator which is connected, on the one hand to the vapour chamber of the water container and on the other hand to the nozzle by means of a pipe.

The vapour emerging from the water container into the expansion chamber is freed from water drops produced by condensation so that only between the separator and the outlet nozzle is there the danger of the formation of condensation water. By suitable disposition of the pipe to the nozzle and construction of the nozzle emergence of this condensation water can be avoided. Furthermore, impurities present and carried in the vapour can be separated in the separator so that these also can be prevented from reaching the nozzle. With ordinary water there are no disturbances. Should the water foam, due to contamination, for example, with soap or the like, and the foam be expelled from the water container into the expansion chamber, then the foam falls into this chamber so that it can also be prevented from reaching the nozzle. Finally there is the possibility of adding materials to the water and in fact even those materials which foam very much since this foam also falls into the expansion chamber whilst the materials, such as perfume, and materials possibly present in vapour form, pass with the vapour to the outlet nozzle.

According to a preferred embodiment of the invention, the expansion chamber may be connected to the water container via a return pipe. By means of this return pipe liquid, for example, water, with any materials present in the expansion chamber, can be guided back again into the water container and can be re-evaporated there so that on the one hand the water supply lasts longer and on the other hand the materials need not remain unused.

The invention will now be described further by way of example only and with reference to the accompanying drawing which is a diagrammatic representation of one embodiment of the invention.

In the drawing parts not essential for an understanding of the invention have been omitted, in particular in so far as the cladding of the apparatus is concerned.

The drawing shows a stand 1 on which the essential parts of the apparatus are fitted, and an upper cover plate 2. On a cross bearer 3 of the stand 1 a water container 4 is detachably fixed which can be filled via a pipe 5 from the cover plate 2 from a funnel disposed there. For this purpose a connection piece 7 of the pipe 5 penetrates deeply into the container 4. Furthermore, in the water container 4 there is suspended an evaporation apparatus, for example, in the form of an electrical immersion boiler 6 the electrical supply for which is not shown. One the cross bearer 3 of the stand 1 there is furthermore detachably fixed a vessel 8 forming an expansion chamber which, as is also the case with the water container 4 consists for example of a transparent material. The vessel 8 is in communication with the vapour chamber 10 of the water container 4 via a pipe 9. The pipe 9 leads freely into the vessel 8.

On the vessel 8 there is furthermore connected a pipe 11 which passes upwardly through the cover plate 2 and has an upwardly inclined section 12 which passes through an ozone producer, for example, a UV burner 13. Vapour led through the pipe 11, 12 takes along ozone gas from the chamber 13 so that from the nozzle 14 a water vapour/ozone gas mixture emerges.

On the bottom of the vessel 8 is connected a return pipe 15 which leads via an inserted control member 16 with a section 17 thereof the filling pipe 5 for the water container 4.

During operation of the apparatus, the water 18 present in the container 4 is evaporated and the vapour passes over from the vapour chamber 10 via the pipe 9 into the vessel 8. There, any condensation water present in the stream and any foam carried with it are separated at 19 so that via the pipe 11, 12, only pure water vapour reaches the ozone chamber 13. The liquid 19 falling into the vessel 8, which may contain impurities or non-evaporated materials, is led back via the pipes 15 and 17 into the water container 4. The starting materials are pre-mixed with water and the mixture introduced into the water container 4 via the filling pipe 5.

What is claimed is:

1. Apparatus, for dermatological treatment with a water vapor/ozone gas mixture, comprising a water container, an evaporation device for evaporating water in said container, an ozone gas producer, a nozzle connected to said water container and to said ozone gas producer for spraying a water vapor/ozone gas mixture, and an expansion chamber means, interposed between the water container and the nozzle, for enabling separation of non-vaporous additive or containment material from the water vapor fed to the nozzle, said expansion chamber means being provided with inlet means for freely admitting said water vapor and non-vaporous material into said expansion chamber means from said water container and vapor outlet means for enabling said water vapor to pass from said expansion chamber means to the nozzle.

2. Apparatus according to claim 1, wherein said nozzle is connected to said water container by an upwardly directed pipe.

3. Apparatus according to claim 1, wherein the expansion chamber means is also connected to the water container via a return pipe for returning separated material to the water container.

4. Apparatus according to claim 1, characterized in that the expansion chamber is formed by a closed vessel having said inlet means and the vapor outlet means at its upper end.

* * * * *